United States Patent [19]

Okada et al.

[11] Patent Number: 4,778,913

[45] Date of Patent: Oct. 18, 1988

[54] PEROXYDICARBONATE CONTAINING NON-CONJUGATE TYPE UNSATURATED BOND

[75] Inventors: Yuji Okada, Aichi; Kenji Kato, Tokorozawa; Motoyuki Sugiura, Aichi, all of Japan

[73] Assignee: Nippon Oils & Fats Co., Ltd., Tokyo, Japan

[21] Appl. No.: 930,395

[22] Filed: Nov. 14, 1986

[30] Foreign Application Priority Data

Nov. 14, 1985 [JP] Japan .................................. 60-253834

[51] Int. Cl.$^4$ .............................................. C07C 179/14
[52] U.S. Cl. ..................................... 558/264; 526/209
[58] Field of Search ........................................... 558/264

[56] References Cited

U.S. PATENT DOCUMENTS 2,370,588 3/1945 Strain .................................. 558/264

4,269,726 5/1981 Kolczynski et al. ................. 558/264

FOREIGN PATENT DOCUMENTS 2317788 3/1974 Fed. Rep. of Germany ...... 558/264

*Primary Examiner*—Vivian Garner
*Attorney, Agent, or Firm*—Oblon, Fisher, Spivak, McClelland & Maier

[57] ABSTRACT

A novel peroxydicarbonate containing a non-conjugate type unsaturated bond, represented by the general formula:

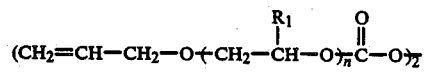

(wherein $R_1$ stands for a hydrogen atom or a methyl group and n for an integer of the value of 1 or 2) is particularly useful as a polymerization initiator.

5 Claims, No Drawings

PEROXYDICARBONATE CONTAINING NON-CONJUGATE TYPE UNSATURATED BOND

FIELD OF THE INVENTION AND RELATED ART STATEMENT

This invention relates to a novel peroxydicarbonate containing a non-conjugate type unsaturated bond. This peroxydicarbonate is a useful compound as a polymerization initiator.

As a peroxydicarbonate containing a non-conjugate unsaturated bond, the allyl peroxydicarbonate represented by the formula:

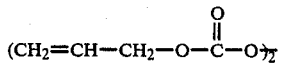

has been reported in the Journal of the American Chemical Society, Vol. 72, p. 1254 (1950). It has been known that this allyl peroxydicarbonate retains its activity at low temperatures, that it possesses a non-conjugate type double bond, that, when it is used as a polymerization initiator for a non-conjugate type monomer such as, for example, vinyl chloride, therefore, the polymerization produces a branched polymer, and that it is useful for the production of a polymer of a high molecular weight with improved workability (Report of the 35th Forum on Polyvinyl Chloride (PVC)).

When the allyl peroxydicarbonate mentioned above as a known peroxydicarbonate is used as a polymerization initiator, the efficiency of the compound as an initiator is not sufficient and the safety thereof in the process of handling is not sufficiently high. For this compound to be produced safely, it must be produced in the presence of a suitable diluent, as in the form diluted in a concentration of about 40% in toluene for commercial production.

OBJECT AND SUMMARY OF THE INVENTION

An object of this invention is to provide a novel peroxydicarbonate containing a non-conjugate type unsaturated bond, which retains its activity at low temperatures and exhibits heretofore unattained efficiency and safety as a polymerization initiator. The inventors have conducted various studies in search of a novel peroxydicarbonate serving as an initiator with improved efficiency and safety. This invention has been perfected as the result.

The novel peroxydicarbonate containing a non-conjugate type unsaturated bond of the invention which has fulfilled the object described above is represented by the following general formula.

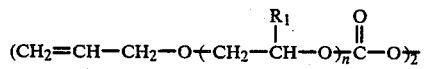

(wherein $R_1$ stands for a hydrogen atom or a methyl group and n for an integer of the value of 1 or 2).

DETAILED DESCRIPTION OF THE PREFERRED EMBODIMENT

First, specific non-conjugate type unsaturated bond-containing peroxydicarbonates of this invention and their theoretical active oxygen contents are shown below.

| Peroxydicarbonate of this invention | | | Theoretical active oxygen content (%) |
|---|---|---|---|
| (1) | $R_1$ = Hydrogen atom | n = 1 | 5.51 |
| $(CH_2=CH-CH_2-O-CH_2-CH_2-O-\overset{O}{\underset{\|}{C}}-O)_2$ | | | |
| (2) | $R_1$ = Methyl group | n = 1 | 5.03 |
| $(CH_2=CH-CH_2-O-CH_2-\overset{CH_3}{\underset{\|}{CH}}-O-\overset{O}{\underset{\|}{C}}-O)_2$ | | | |
| (3) | $R_1$ = Hydrogen atom | n = 2 | 4.23 |
| $(CH_2=CH-CH_2-O-CH_2-CH_2-O-CH_2-CH_2-O-\overset{O}{\underset{\|}{C}}-O)_2$ | | | |
| (4) | $R_1$ = Methyl group | n = 2 | 3.68 |
| $(CH_2=CH-CH_2-O-CH_2-\overset{CH_3}{\underset{\|}{CH}}-O-CH_2-\overset{CH_3}{\underset{\|}{CH}}-O-\overset{O}{\underset{\|}{C}}-O)_2$ | | | |

Such a novel non-conjugate type unsaturated bond-containing peroxydicarbonate of the present invention as described above can be produced as shown below.

It is easily obtained by adding gradually with continued agitation a chloroformate resulting from the reaction of ethylene glycol monoallyl ether, isopropylene glycol monoallyl ether, diethylene glycol monoallyl ether or diisopropylene glycol monoallyl ether with phosgene to an aqueous solution of a peroxidizing agent such as sodium peroxide or potassium peroxide to induce reaction and, after completion of the reaction, separating the reaction product from the resulting reaction mixture. In this case, the amount of the peroxidizing agent to be used is approximately in the range of 0.5 to 1.5 mols per mol of the chloroformate. The reaction conditions are similar to those used for the production of the aforementioned known peroxydicarbonate, the reaction temperature is in the range of $-10°$ to 20° C., preferably $-5°$ to 10° C., and the reaction time is approximately in the range of 1 to 5 hours, preferably 1.5 to 3 hours.

The novel non-conjugate type unsaturated bond-containing peroxydicarbonate of the present invention is a transparent liquid at normal room temprature.

The structure of the novel non-conjugate type unsaturated bond-containing peroxydicarbonate of this invention can be confirmed by refining the compound by column chromatography, testing the refined compound for active oxygen content by iodometry, analyzing the absorptions of $CH_2=CH-CH_2-$, $-CH_2-O-CH_2-$, $-O-C(O)-O-$, and $-OO-$ bonds by infrared absorption spectrometry and the absorption spectra and the intensities of $CH_2=CH-CH_2-$, $-CH_2-CH_2-$, and $-CH_2-CH(CH_3)-$ bonds by proton-nuclear magnetic resonance, and examining the elementary analyses of the compound.

This novel non-conjugate type unsaturated bond-containing peroxydicarbonate is useful as a polymerization initiator as described above. The novel non-conjugate type unsaturated bond-containing peroxydicarbonate of this invention possesses the following advantages over the known non-conjugate type unsaturated bond-containing allyl peroxydicarbonate.

(1) It exhibits high efficiency in the initiation of polymerization.
(2) Because of its weak power of explosion or destruction, it can be handled with high safety.
(3) Owing to the improved safety, it can be synthesized without use of a solvent and enjoys satisfactory productivity.

Now, the present invention will be described more specifically below with reference to working examples and comparative experiments.

EXAMPLE 1

In a four-necked flask provided with a stirrer and a thermometer, 415 g (0.3 mol) of an aqueous 10% potassium carbonate solution was mixed with 10.8 g (0.3 mol) of an aqueous 50% hydrogen peroxide solution to prepare an aqueous potassium peroxide solution. Then, the aforementioned aqueous potassium peroxide solution was kept stirred at a temperature in the range of 0° to 5° C., and 82 g (0.5 mol) of chloroformate (purity 95.0% by weight) of ethylene glycol monoallyl ether was added piecemeal over a period of 20 minutes. Thereafter, the stirring was continued at a temperature in the range of 3° to 5° C. for 90 minutes to induce a reaction. After completion of this reaction, the oil layer was removed from the resulting reaction mixture with the aid of a separating funnel. The oil phase was washed with water twice and then dried with anhydrous magnesium sulfate. The resulting phase was filtered to remove solids and obtain 64.2 g of a transparent viscous liquid. By conventional iodometry, this viscous liquid was found to have an active oxygen content of 5.36%. Then, this viscous liquid was refined by column chromatography. The refined liquid, by iodometry, was found to have an active oxygen content of 5.51%.

In the infrared absorption spectrum of this liquid, the characteristic absorption frequencies were 1780 cm$^{-1}$, 1810 cm$^{-1}$ (C=O of carbonyl group), 1640 cm$^{-1}$, 1420 cm$^{-1}$ (CH$_2$CH—CH$_2$—bond of allyl group), 1120 cm$^{-1}$ (—CH$_2$—O—CH$_2$ bond, and 890 cm$^{-1}$ (—OO— bond). The δ vaues and intensities of the nuclear magnetic resonance spectrum were as follows.

| 5.30 ppm | (4 H) | ⓐ |
| 5.95 ppm | (2 H) | ⓑ |
| 4.05 ppm | (4 H) | ⓒ |
| 3.70 ppm | (4 H) | ⓓ |
| 4.50 ppm | (4 H) | ⓔ |

In the elementary analyses, C 49.3%, H 6.2%, and O 44.5% were found.

The values found in the aforementioned nuclear magnetic resonance spectrum represent the component structures of the chemical formula of peroxydicarbonate of this invention shown below. Further, the numerical values of the elementary analyses agree well with the respective theoretical values, C 49.65%, H 6.25%, and O 44.09%.

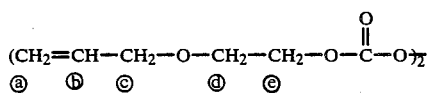

$$(CH_2=CH-CH_2-O-CH_2-CH_2-O-\overset{O}{\underset{\|}{C}}-O)_2$$
ⓐ      ⓑ      ⓒ         ⓓ      ⓔ

Thus, the viscous liquid obtained in this example was identified to be the peroxydicarbonate of this invention represented by the aforementioned formula. The purity of the peroxydicarbonate before the refinement was 97.3%, the yield was 86.1%, and the purity thereof after the refinement was 100%. The results are shown in Table 1.

Then, the peroxydicarbonate of this invention was tested for safety by the following methods.

Test for safety

The compound was subjected to ballistic mortar test, pressure container test, and explosive test by the following methods which are indicated in "Safety Engineering", Vol. 4, No. 2, p. 181 (1965). The results were as shown in Table 2. Ballistic mortar test:

In a space hermetically closed with iron blocks to a high degree, a 10-g sample was exploded with a detonator, No. 6. The explosive force generated by the exploded sample was measured relative to the explosive force of trinitrotoluene (TNT) taken as 100.

Pressure container test

In a stainless steel container having an inner volume of 200 ml, a 5-g sample was thermally decomposed under a fixed set of conditions and the diameter of the smallest possible orifice sufficient to maintain the inner pressure of the container at a fixed level of 10 kg/cm2 was measured. This test serves to evaluate the degree of vigor with which the sample is decomposed.

Explosive test

In an iron gas pipe 27 mm in inside diameter and 250 mm in length, a sample (about 100 g) was exploded with 2 g of trinitrotoluene (TNT) and a detonator, No. 6. The degree of destruction caused on the gas pipe was evaluated by comparing the used gas pipe with a blank, to determine whether the sample had exploded or not.

EXAMPLE 2

The procedure of Example 1 was followed, except that 96.0 g (0.5 mol) of chloroformate (purity 93%) of isopropylene glycol monoallyl ether was used in place of chloroformate of ethylene glycol monoallyl ether. Consequently, 69.3 g of a transparent colorless liquid was obtained. By conventional iodometry this liquid was found to have an active oxygen content of 4.84%. This liquid was refined by column chromatography. The refined compound was found by iodometry to have an active oxygen content of 5.03%. In the infrared absorption spectrum of this compound, the characteristic absorption wavelengths were 1780 cm$^{-1}$, 1810 cm$^{-1}$ (C=O bond of carbonyl group), 1640 cm$^{-1}$, 1420 cm$^{-1}$ (CH$_2$CH—CH$_2$—bond of allyl group), 1120 cm$^{-1}$ (—CH$_2$—O—CH$_2$— bond), and 890 cm$^{-1}$ (—OO— bond). The δ values and intensities of the nuclear magnetic resonance spectrum were as follows.

| 5.30 ppm | (4 H) | ⓐ' |
| 5.95 ppm | (2 H) | ⓑ' |
| 4.05 ppm | (4 H) | ⓒ' |
| 3.80 ppm | (4 H) | ⓓ' |
| 5.10 ppm | (2 H) | ⓔ' |
| 1.15 ppm | (6 H) | ⓕ' |

In the elementary analyses, C 52.6%, H 6.9%, and O 40.5% were found. The values found in the aforementioned nuclear magnetic resonance spectrum represent the component structures of the chemical formula of the peroxydicarbonate of this invention shown below. Further, the numerical values of the elementary analyses agree well with the respective theoretical values, C 52.83%, H 6.96%, and O 40.21%.

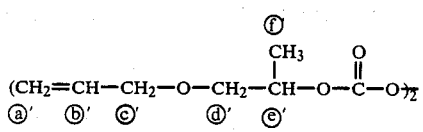

Thus, the viscous liquid obtained in this example was identified to be the peroxydicarbonate of this invention represented by the aforementioned formula. The purity of the peroxydicarbonate before the refinement was 95.1%, the yield was 82.8%, and the purity thereof after the refinement was 100%. The results were as shown in Table 1.

Similarly to Example 1, the compound was tested for safety. The results were as shown in Table 2.

EXAMPLE 3

The procedure of Example 1 was repeated, except that 110.0 g (0.5 mol) of chloroformate (purity 93%) of diethylene glycol monoallyl ether (purity 93.9%) was used in place of chloroformate of ethylene glycol monoallyl ether. Consequently, there was obtained 84.2 g of a transparent colorless viscous liquid. This liquid was found by conventional iodometry to have an active oxygen content of 4.00%. This liquid was refined by column chromatography. By iodometry the refined compound was found to have an active oxygen content of 4.22%.

In the infrared absorption spectrum of this liquid, the characteristic absorption wavelengths were 1780 cm$^{-1}$, 1810 cm$^{-1}$ (C=O bond of carbonyl group), 1650 cm$^{-1}$, 1420 cm$^{-1}$ (CH$_2$=CH—CH$_2$—bond of allyl group), 1120 cm$^{-1}$ (—CH$_2$—O—CH$_2$— bond), and 890 cm$^{-1}$ (—OO— bond). The δ values and intensities of the nuclear magnetic resonance spectrum were as follows.

| | | |
|---|---|---|
| 5.30 ppm | (4 H) | ⓐ'' |
| 5.95 ppm | (2 H) | ⓑ'' |
| 4.05 ppm | (4 H) | ⓒ'' |
| 3.65 ppm | (8 H) | ⓓ'' |
| 3.75 ppm | (4 H) | ⓔ'' |
| 4.50 ppm | (4 H) | ⓕ'' |

In the elementary analyses, C 50.5%, H 6.8%, and O 42.7% were found. The values found in the aforementioned nuclear magnetic resonance spectrum represent the component structures of the chemical formula of the peroxydicarbonate of this invention shown below. Further, the numerical values of the elementary analyses agree well with the theoretical values, C 50.79%, H 6.93%, and O 42.28%.

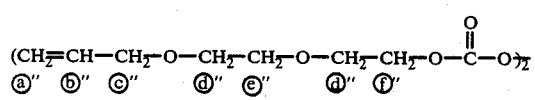

Thus, the viscous liquid obtained in a refined state in this example was identified to be the peroxydicarbonate of this invention represented by the aforementioned formula. The purity of the peroxydicarbonate before the refinement was 94.5%, the yield was 84.2%, and the purity thereof after the refinement was 99.7%. The results were as shown in Table 1.

Similarly to Example 1, the compound was tested for safety. The results were as shown in Table 2.

EXAMPLE 4

The procedure of Example 1 was followed, except that 130.8 g (0.5 mol) of chloroformate (purity 90.4%) of diisopropylene glycol monoallyl ether was used in place of chloroformate of ethylene glycol monoallyl ether. Consequently, there was obtained 97.3 g of a transparent colorless viscous liquid. By conventional iodometry this liquid was found to have an active oxygen content of 3.41%. This liquid was refined by column chromatography. By iodometry the refined compound was found to have an active oxygen content of 3.67%.

In the infrared absorption spectrum of this compound, the characteristic absorption wavelengths were 1780 cm$^{-1}$, 1810 cm$^{-1}$ (C=O bond of carbonyl group), 1640 cm$^{-1}$, 1420 cm$^{-1}$ (CH$_2$CH—CH$_2$—bond of allyl group), 1120 cm$^{-1}$ (—CH$_2$—O—CH$_2$— bond), and 890 cm$^{-1}$ (—OO— bond). The δ values and intensities of the nuclear magnetic resonance spectrum were as follows.

| | | |
|---|---|---|
| 5.30 ppm | (4 H) | ⓐ''' |
| 5.95 ppm | (2 H) | ⓑ''' |
| 4.05 ppm | (4 H) | ⓒ''' |
| 3.70 ppm | (4 H) | ⓓ''' |
| 4.50 ppm | (2 H) | ⓔ''' |
| 1.14 ppm | (12 H) | ⓕ''' |
| 3.80 ppm | (4 H) | ⓖ''' |
| 5.10 ppm | (2 H) | ⓗ''' |

In the elementary analyses, C 55.0%, H 7.7%, and O 37.3% were found. The values of the aforementioned nuclear magnetic resonance spectrum represent the component structures of the chemical compound of the peroxydicarbonate of the present invention shown below. Further, the numerical values of the elementary analyses agree well with the theoretical values, C 55.29%, H 7.89%, and O 36.82%.

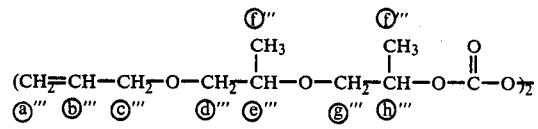

Thus, the viscous liquid obtained in a refined state in this example was identified to be the peroxydicarbonate of this invention shown by the aforementioned formula. The purity of the peroxydicarbonate before the refinement was 92.7%, the yield was 83.1%, and the purity thereof after the refinement was 99.7%. The results were as shown in Table 1.

Similarly to Example 1, the compound was tested for safety. The results were as shown in Table 2.

COMPARATIVE EXPERIMENT

The procedure of Example 1 was repeated, except that 61.5 g (0.5 mol) of allyl chloroformate (purity 97.5%) was used in place of chloroformate of ethylene glycol monoallyl ether and 12 g of toluene was used as a diluent. Consequently, there was obtained 53.1 g of a transparent colorless liquid. By conventional iodometry this liquid was found to have an active oxygen content of 6.21%.

As a result, allyl peroxydicarbonate of a purity of 78.5% was obtained. The results were as shown in Table 1.

This liquid was refined by column chromatography. The refined compound was found by iodometry to have an active oxygen content of 7.87%.

Similarly to Example 1, this compound was tested for safety. The results were as shown in Table 2.

solved as a polymerization initiator in styrene at a rate of 0.02 mol per liter of styrene to prepare test specimens. In a sealed glass ampoule 12 mm in inside diameter, 5 ml of a given specimen was polymerized at 60° C. to find the efficiency of the compound as an initiator.

The efficiency was determined by the following method indicated in "Method of Experiment on Polymerization of Vinyl" (published by Kyoritsu Publish-

TABLE 1

| | Specific peroxydicarbonate | Before refinement | | | After refinement | | Theoretical active oxygen content (%) |
|---|---|---|---|---|---|---|---|
| | | Active oxygen content | Purity (%) | Yield (%) | Active oxygen content | Purity (%) | |
| Example 1 | $(CH_2=CH-CH_2-O-CH_2-CH_2-O-\overset{O}{\underset{\parallel}{C}}-O)_2$ | 5.36 | 97.3 | 86.1 | 5.51 | 100 | 5.51 |
| Example 2 | $(CH_2=CH-CH_2-O-CH_2-\overset{CH_3}{\underset{\vert}{CH}}-O-\overset{O}{\underset{\parallel}{C}}-O)_2$ | 4.78 | 95.1 | 82.8 | 5.03 | 100 | 5.03 |
| Example 3 | $(CH_2=CH-CH_2-O-CH_2-CH_2-O-CH_2-CH_2-O-\overset{O}{\underset{\parallel}{C}}-O)_2$ | 4.00 | 94.5 | 84.2 | 4.22 | 99.7 | 4.23 |
| Example 4 | $(CH_2=CH-CH_2-O-CH_2-\overset{CH_3}{\underset{\vert}{CH}}-O-CH_2-\overset{CH_3}{\underset{\vert}{CH}}-O-\overset{O}{\underset{\parallel}{C}}-O)_2$ | 3.41 | 92.7 | 83.1 | 3.67 | 99.7 | 3.68 |
| Comparative Experiment | $(CH_2=CH-CH_2-O-\overset{O}{\underset{\parallel}{C}}-O)_2$ | 6.21 | 78.5 | 82.5 | 7.87 | 99.5 | 7.91 |

TABLE 2

| | Specific peroxydicarbonate | Ballistic mortar test (relative of TNT) | Pressure container test (mm) | Explosive property |
|---|---|---|---|---|
| Example 1 | $(CH_2=CH-CH_2-O-CH_2-CH_2-O-\overset{O}{\underset{\parallel}{C}}-O)_2$ | 0.5 | 0 | No |
| Example 2 | $(CH_2=CH-CH_2-O-CH_2-\overset{CH_3}{\underset{\vert}{CH}}-O-\overset{O}{\underset{\parallel}{C}}-O)_2$ | 0.4 | 0 | No |
| Example 3 | $(CH_2=CH-CH_2-O-CH_2-CH_2-O-CH_2-CH_2-O-\overset{O}{\underset{\parallel}{C}}-O)_2$ | 0.4 | 0 | No |
| Example 4 | $(CH_2=CH-CH_2-O-CH_2-\overset{CH_3}{\underset{\vert}{CH}}-O-CH_2-\overset{CH_3}{\underset{\vert}{CH}}-O-\overset{O}{\underset{\parallel}{C}}-O)_2$ | 0.4 | 0 | No |
| Comparative Experiment | $(CH_2=CH-CH_2-O-\overset{O}{\underset{\parallel}{C}}-O)_2$ | 19.3 | 20.7 | Yes |

The results of Table 2 indicate that the peroxydicarbonate of the present invention excels in safety as compared with the allyl peroxydicarbonate known to the art.

Referential Example (Test for polymerization (bulk polymerization) of styrene and efficiency as initiator)

The non-conjugate type unsaturated bond-containing peroxydicarbonate compounds obtained in Examples 1–4 and Comparative Experiment were severally dising), page 256.

Specifically, the determination of the efficiency as an initiator is obtained by finding the total polymerization speed R, inducing the speed of initiation Ri from the speed R, and calculating the efficiency of an initiator f in accordance with the basic formula Ri=2Kdf(I) (wherein kd stands for the decomposition speed constant of the initiator and (I) for the concentraton of the initiator).

The results are shown in Table 3.

TABLE 3

| | Specific peroxydicarbonate | Efficiency of initiator |
|---|---|---|
| Example 1 | $(CH_2=CH-CH_2-O-CH_2-CH_2-O-\underset{\underset{O}{\|\|}}{C}-O)_{\overline{2}}$ | 0.45 |
| Example 2 | $(CH_2=CH-CH_2-O-CH_2-\underset{\underset{CH_3}{\|}}{CH}-O-\underset{\underset{O}{\|\|}}{C}-O)_{\overline{2}}$ | 0.43 |
| Example 3 | $(CH_2=CH-CH_2-O-CH_2-CH_2-O-CH_2-CH_2-O-\underset{\underset{O}{\|\|}}{C}-O)_{\overline{2}}$ | 0.41 |
| Example 4 | $(CH_2=CH-CH_2-O-CH_2-\underset{\underset{CH_3}{\|}}{CH}-O-CH_2-\underset{\underset{CH_3}{\|}}{CH}-O-\underset{\underset{O}{\|\|}}{C}-O)_{\overline{2}}$ | 0.42 |
| Comparative Experiment | $(CH_2=CH-CH_2-O-\underset{\underset{O}{\|\|}}{C}-O)_{\overline{2}}$ | 0.26 |

It is noted from Table 3 that the compounds of the working examples showed higher levels of efficiency than the compound of the comparative experiment. The results clearly indicate that the peroxydicarbonate compounds of this invention are more useful as a polymerization initiator than the allyl peroxydicarbonate known to the art.

What is claimed is:

1. A peroxydicarbonate having the formula:

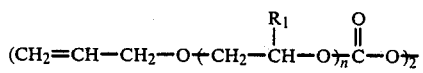

wherein $R_1$ is a hydrogen atom or a methyl group and n is an integer of 1 or 2.

2. The peroxydicarbonate according to claim 1, which has the following formula:

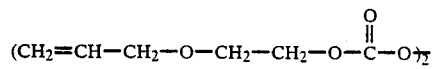

3. The peroxydicarbonate according to claim 1, which has the following formula:

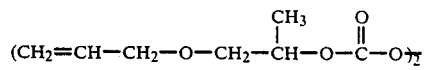

4. The peroxydicarbonate according to claim 1, which has the following formula:

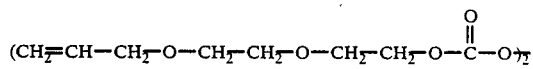

5. The peroxydicarbonate according to claim 1, which has the following formula:

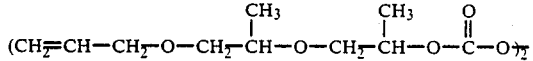

* * * * *